United States Patent
Palma et al.

(10) Patent No.: US 7,374,927 B2
(45) Date of Patent: May 20, 2008

(54) METHODS OF ANALYSIS OF DEGRADED NUCLEIC ACID SAMPLES

(75) Inventors: John F. Palma, San Ramon, CA (US); Eric B. Schell, Mountain View, CA (US); Alan J. Williams, Albany, CA (US)

(73) Assignee: Affymetrix, Inc., Santa Clara, CA (US)

( * ) Notice: Subject to any disclaimer, the term of this patent is extended or adjusted under 35 U.S.C. 154(b) by 133 days.

(21) Appl. No.: 11/121,849

(22) Filed: May 3, 2005

(65) Prior Publication Data

US 2005/0272080 A1    Dec. 8, 2005

Related U.S. Application Data

(60) Provisional application No. 60/567,949, filed on May 3, 2004.

(51) Int. Cl.
*C12M 1/34* (2006.01)
*C12M 3/00* (2006.01)
*C07H 21/04* (2006.01)
*C12Q 1/68* (2006.01)

(52) U.S. Cl. .................. 435/287.2; 435/91.1; 435/6; 536/23.1; 536/24.3

(58) Field of Classification Search .................. None
See application file for complete search history.

(56) References Cited

U.S. PATENT DOCUMENTS

| | | | |
|---|---|---|---|
| 5,800,992 A | | 9/1998 | Fodor et al. |
| 5,837,832 A | | 11/1998 | Chee et al. |
| 6,133,436 A | * | 10/2000 | Koster et al. ............... 536/24.3 |
| 6,582,906 B1 | | 6/2003 | Cao et al. |
| 2001/0051344 A1 | * | 12/2001 | Shalon et al. .................. 435/6 |
| 2001/0053519 A1 | * | 12/2001 | Fodor et al. ..................... 435/6 |
| 2002/0009738 A1 | | 1/2002 | Zehantner et al. |
| 2003/0143593 A1 | | 7/2003 | Hermitte et al. |
| 2003/0198983 A1 | | 10/2003 | Zhou |
| 2003/0207312 A1 | | 11/2003 | Sorge |
| 2003/0236633 A1 | | 12/2003 | Mei et al. |
| 2005/0014168 A1 | | 1/2005 | Erlander et al. |

OTHER PUBLICATIONS

Dudin G et al 'Sorting of chromosomes by magnetic separation.' Hum Genet. Oct. 1988;80(2):111-6.*
Svensson A-C et al 'Chromosomal distribution, localization and expression of the human endogenous retrovirus ERV9.' Cytogenet Cell Genet. 2001;92(1-2):89-96.*
Deb-Rinker P et al 'Molecular characterization of a 2.7-kb, 12q13-specific, retroviral-related sequence isolated by RDA from monozygotic twin pairs discordant for schizophrenia.' Genome. Apr. 2002;45(2):381-90.*
Affymetrix Product Catalog 2002 and GenChip Human Genome U95 Set, available from www.affymetrix.com, 4 pages.*
Details for HG-U95AV2:40846_G_AT, available from www.affymetrix.com, pp. 1-5.*
Details for HG_U95AV2:38267_AT, available from www.affymetrix.com, pp. 1-7.*
GenBank Locus NM_004170, available from www.ncbi.nlh.nih.gov, pp. 1-5.*
GenBank Locus AF167570, available from www.ncbi.nlh.nih.gov, pp. 1-3.*
Godfrey TE et al 'Quantitative mRNA expression analysis from formalin-fixed, paraffin-embedded tissues using 5' nuclease quantitative reverse transcription-polymerase chain reaction.' J Mol Diagn. May 2000;2(2):84-91.*
D'mell V et al 'Alternative mRNA polyadenylation can potentially affect detection of gene expression by affymetrix genechip arrays.' Appl Bioinformatics. 2006;5(4):249-53.*
Cheung VG et al 'Natural variation in human gene expression assessed in lymphoblastoid cells.' Nat Genet. Mar. 2003;33(3):422-5.*
Affymetrix, Inc. "Array Design for the GENECHIP Human Genome U133 Set", Gene Expression Monitoring Technical Note, Product No. 701133 Rev. 1 (2001) p. 1-10.
Affymetrix, Inc. "Performance and Validation of the GENECHIP Human Genome U133 Set", Gene Expression Monitoring-Technical Note Product No. 701211 Rev. 1, (2002) p. 1-10.
Lockhart et al. "Expression monitoring by hybridization to high-density oligonucleotide arrays", Nature Biotech. 14:1675-1680 (1996).

* cited by examiner

*Primary Examiner*—Jehanne Sitton
*Assistant Examiner*—Stephen Kapushoc
(74) *Attorney, Agent, or Firm*—Sandra E. Wells

(57) ABSTRACT

The invention provides arrays for analysis of compromised nucleic acid samples, for example, nucleic acids obtained from formalin fixed paraffin embedded samples and methods to analyzed these compromised samples. Arrays are disclosed in which the probe selection region used to select probes for the array is the 300 bases of the target MRNA that are immediately upstream of the start of the poly(A) tail of the mRNA. The probes selected for the array are more biased toward the 3' end of the mRNA than other arrays that are currently available.

4 Claims, No Drawings

METHODS OF ANALYSIS OF DEGRADED NUCLEIC ACID SAMPLES

RELATED APPLICATIONS

This application claims the benefit of U.S. Provisional Application No. 60/567,949 filed May 3, 2004. The entire disclosure of the above applications is incorporated herein by reference in its entirety for all purposes.

FIELD OF THE INVENTION

The present invention provides a method of analyzing nucleic acid samples that may be degraded, for example, formalin fixed paraffin embedded samples. Methods of selecting probes and arrays of probes are provided. A unique pool of nucleic acid sequences useful for analyzing degraded human nucleic acid samples is provided. The invention therefore relates to diverse fields impacted by the nature of molecular interaction, including chemistry, biology, medicine, and medical diagnostics.

REFERENCE TO SEQUENCE LISTING

The Sequence Listing submitted on compact disk is hereby incorporated by reference. The file on the disk is named 3684.1seqlist the file is 96.3 MB and the date of creation is May 3, 2005.

BACKGROUND OF THE INVENTION

Many biological functions are carried out by regulating the expression levels of various genes, either through changes in levels of transcription (e.g. through control of initiation, provision of RNA precursors, RNA processing, etc.) of particular genes, through changes in the copy number of the genetic DNA, through changes in RNA processing such as polyadenylation and splicing or RNA stability or through changes in protein synthesis. Changes in the expression levels of particular genes (e.g. oncogenes or tumor suppressors), serve as signposts for the presence and progression of various diseases.

Gene expression analysis using microarrays allows study of entire expressed genomes and has led to insights into the involvement of diverse molecular interactions as well as the pathologies that result from their disruption. Microarrays have been used to distinguish between pathologically similar diseases such as Acute Myeloblastic Leukemia and Acute Lymphoblastic Leukemia, Golub et al. *Science,* 286 (5439), 531-7 (1999), to provide insight into inflammatory diseases such as psoriasis and systemic lupus erythematosus (SLE), see for example, Zhou et al. *Physiological Genomics,* 13(1), 69-78, (2003) and to study diseases such as diabetes, Mootha et al. *Nature Genetics,* 34, 267-273 (2003).

SUMMARY OF THE INVENTION

An array comprising each of the sequences listed in SEQ ID NO: 1-673,904 is disclosed. In a preferred embodiment each of the sequences is present on the array in a known location. Each of the sequences of the sequence listing is present in a distinct feature and the location of a given probe is known or determinable. Control sequences may also be present on the array. The probes may be attached to a solid support, such as a glass chip, beads or particles.

In a preferred aspect a nucleic acid sample is amplified by hybridizing a primer to the poly(A) tail and extending the primer with a reverse transcriptase. The resulting first strand cDNA is copies to make double stranded cDNA with an RNA polymerase promoter. An RNA polymerase is used to make multiple RNA copies. The RNA copies are fragmented and hybridized to the array and a hybridization pattern is detected and analyzed to obtain expression measurements for a plurality of mRNA targets.

In some aspects the RNAs that are targeted are sets of 1,000 or more RNAs that share a common feature, for example, they may all be differentially expressed between a cancerous sample and a normal, non-cancerous sample. The probe sets for most of the targets consist of probes from the 300 bases immediately 5' of the polyA tail.

DETAILED DESCRIPTION OF THE INVENTION a) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual,* and *Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, *Prin-*

*ciples of Biochemistry* 3rd Ed., W. H. Freeman Pub., New York, N.Y. and Berg et al. (2002) *Biochemistry*, 5th Ed., W. H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT applications Ser. Nos. PCT/US99/00730 (International Publication No. WO 99/36760) and PCT/US01/04285 (International Publication No. WO01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®). Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. patent application publication 20030036069), and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, for example, *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 and U.S. Ser. No. 09/513,300, which are incorporated herein by reference.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA*, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. No. 6,361,947, 6,391,592 and U.S. Ser. Nos. 09/916,135, 09/920,491 (U.S. patent application publication 20030096235), U.S. Ser. No. 09/910,292 (U.S. patent application publication 20030082543), and 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* (2nd Ed. Cold Spring Harbor, N.Y., 1989); Berger and Kimmel *Methods in Enzymology*, Vol. 152, *Guide to Molecular Cloning Techniques* (Academic Press, Inc., San Diego, Calif., 1987); Young and Davism, *P.N.A.S*, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Ser. Nos. 10/389,194, 60/493,495 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics*

*Basics: Application in Biological Science and Medicine* (CRC Press, London, 2000) and Ouelette and Bzevanis *Bioinformatics: A Practical Guide for Analysis of Gene and Proteins* (Wiley & Sons, Inc., 2$^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Ser. Nos. 10/97,621, 10/063,559 (U.S. publication No. 20020183936), U.S. Ser. Nos. 10/065,856, 10/065,868, 10/328,818, 10/328,872, 10/423,403, and 60/482,389. All references, patents and patent applications sited herein are incorporated by reference for all purposes.

b) Definitions

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "array plate" as used herein refers to a body having a plurality of arrays in which each microarray is separated by a physical barrier resistant to the passage of liquids and forming an area or space, referred to as a well, capable of containing liquids in contact with the probe array.

The term "biomonomer" as used herein refers to a single unit of biopolymer, which can be linked with the same or other biomonomers to form a biopolymer (for example, a single amino acid or nucleotide with two linking groups one or both of which may have removable protecting groups) or a single unit which is not part of a biopolymer. Thus, for example, a nucleotide is a biomonomer within an oligonucleotide biopolymer, and an amino acid is a biomonomer within a protein or peptide biopolymer; avidin, biotin, antibodies, antibody fragments, etc., for example, are also biomonomers.

The terms "biopolymer" and "biological polymer" as used herein are intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above.

The term "biopolymer synthesis" as used herein is intended to encompass the synthetic production, both organic and inorganic, of a biopolymer. Related to a bioploymer is a "biomonomer".

The term "cartridge" as used herein refers to a body forming an area or space referred to as a well wherein a microarray is contained and separated from the passage of liquids.

The term "combinatorial synthesis strategy" as used herein refers to a combinatorial synthesis strategy is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference. In some aspects the probes of the array are completely complementary to the target sequence over the length of the probe. A 25 base probe, for example would be complementary over that 25 bases to a contiguous 25 bases of the target. The target may be longer than 25 bases.

The term "effective amount" as used herein refers to an amount sufficient to induce a desired result.

The term "excitation energy" as used herein refers to energy used to energize a detectable label for detection, for example illuminating a fluorescent label. Devices for this use include coherent light or non coherent light, such as lasers, UV light, light emitting diodes, an incandescent light source, or any other light or other electromagnetic source of energy having a wavelength in the excitation band of an excitable label, or capable of providing detectable transmitted, reflective, or diffused radiation.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook, Fritsche and Maniatis. "Molecular Cloning A laboratory Manual" $2^{nd}$ Ed. Cold Spring Harbor Press (1989) which is hereby incorporated by reference in its entirety for all purposes above.

The term "hybridization conditions" as used herein will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

The term "hybridization probes" as used herein are oligonucleotides capable of binding in a base-specific manner to a complementary strand of nucleic acid. Such probes include peptide nucleic acids, as described in Nielsen et al., Science 254, 1497-1500 (1991), and other nucleic acid analogs and nucleic acid mimetics.

The term "hybridizing specifically to" as used herein refers to the binding, duplexing, or hybridizing of a molecule only to a particular nucleotide sequence or sequences under stringent conditions when that sequence is present in a complex mixture (for example, total cellular) DNA or RNA.

The term "initiation biomonomer" or "initiator biomonomer" as used herein is meant to indicate the first biomonomer which is covalently attached via reactive nucleophiles to the surface of the polymer, or the first biomonomer which is attached to a linker or spacer arm attached to the polymer, the linker or spacer arm being attached to the polymer via reactive nucleophiles.

The term "isolated nucleic acid" as used herein mean an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

The term "label" as used herein refers to a luminescent label, a light scattering label or a radioactive label. Fluorescent labels include, inter alia, the commercially available fluorescein phosphoramidites such as Fluoreprime (Pharmacia), Fluoredite (Millipore) and FAM (ABI). See U.S. Pat. No. 6,287,778.

The term "ligand" as used herein refers to a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (for example, opiates, steroids, etc.), hormone receptors, peptides, enzymes, enzyme substrates, substrate analogs, transition state analogs, cofactors, drugs, proteins, and antibodies.

The term "linkage disequilibrium" or sometimes refer by allelic association as used herein refers to the preferential association of a particular allele or genetic marker with a specific allele, or genetic marker at a nearby chromosomal location more frequently than expected by chance for any particular allele frequency in the population. For example, if locus X has alleles a and b, which occur equally frequently, and linked locus Y has alleles c and d, which occur equally frequently, one would expect the combination ac to occur with a frequency of 0.25. If ac occurs more frequently, then alleles a and c are in linkage disequilibrium. Linkage disequilibrium may result from natural selection of certain combination of alleles or because an allele has been introduced into a population too recently to have reached equilibrium with linked alleles.

The term "microtiter plates" as used herein refers to arrays of discrete wells that come in standard formats (96, 384 and 1536 wells) which are used for examination of the physical, chemical or biological characteristics of a quantity of samples in parallel.

The term "mixed population" or sometimes refer by "complex population" as used herein refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

The term "monomer" as used herein refers to any member of the set of molecules that can be joined together to form an oligomer or polymer. The set of monomers useful in the present invention includes, but is not restricted to, for the example of (poly)peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone.

The term "mRNA" or sometimes refer by "MRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the MRNA transcript or a subsequence thereof has ultimately served as a template. Thus, a cDNA reverse transcribed from an MRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the MRNA, cRNA transcribed from the cDNA, DNA amplified from the genes, RNA transcribed from amplified DNA, and the like.

The term "nucleic acid library" or sometimes refer by "array" as used herein refers to an intentionally created collection of nucleic acids which can be prepared either synthetically or biosynthetically and screened for biological activity in a variety of different formats (for example, libraries of soluble molecules; and libraries of oligos tethered to resin beads, silica chips, or other solid supports). Additionally, the term "array" is meant to include those libraries of nucleic acids which can be prepared by spotting nucleic acids of essentially any length (for example, from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "polymorphism" as used herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term probe selection region refers to the region of the target that is used to design probes. The probes in a probe set will generally be complementary to that region. Probes may be designed to be complementary to the mRNA or to be complementary to the opposite strand. The orientation of the probes (sense or antisense) will depend on the nature of the sample that is hybridized to the array, i.e. sense or anitsense. Methods and computer software for probe selection are disclosed, for example in U.S. patent application Ser. Nos. 11/036,498, 11/036,317, 10/738,546, 10/028,416, 10/308, 379, and 11/078,138, each of which is incorporated herein by reference for all purposes.

The term "reader" or "plate reader" as used herein refers to a_device which is used to identify hybridization events on an array, such as the hybridization between a nucleic acid probe on the array and a fluorescently labeled target. Readers are known in the art and are commercially available through Affymetrix, Santa Clara Calif. and other companies. Generally, they involve the use of an excitation energy (such as a laser) to illuminate a fluorescently labeled target nucleic acid that has hybridized to the probe. Then, the reemitted radiation (at a different wavelength than the excitation energy) is detected using devices such as a CCD, PMT, photodiode, or similar devices to register the collected emissions. See U.S. Pat. No. 6,225,625.

The term "receptor" as used herein refers to a molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The term "surface" or "active probe surface" or "target surface" as used herein refers to the area of the microarray to be analyzed with reagents.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

The term "wafer" as used herein refers to a substrate having surface to which a plurality of arrays are bound. In a preferred embodiment, the arrays are synthesized on the surface of the substrate to create multiple arrays that are physically separate. In one preferred embodiment of a wafer, the arrays are physically separated by a distance of at least about 0.1, 0.25, 0.5, 1 or 1.5 millimeters. The arrays that are on the wafer may be identical, each one may be different, or there may be some combination thereof. Particularly preferred wafers are about 8"×8" and are made using the photolithographic process.

The term "well plate" as used herein refers to a body with a plurality of cavities open at both wherein the cavities form an area or space referred to as a well wherein each well will hold an array.

Arrays for Analysis of Compromised Samples

Arrays of short oligonucleotide probes are commonly used for a variety of methods of nucleic acid analysis. The probes which may be, for example, 15 to 100 bases in length, are typically designed to be complementary to a specific target. A preferred array includes multiple different probes that are complementary to each target. The probes may be short, for example 20-30 bases and may target overlapping or non-overlapping regions of the target. If the target is to be amplified using an amplification scheme that is biased toward the 3' end of the target it is preferable to target the 3' region for probe design as that is the region most likely to be amplified and most likely to be detected in the amplification product.

The probes on many arrays such as the Affymetrix human U133 array are designed to detect sequences that are within about 600 bases of the polyA tail. This minimizes bias resulting from 3' based amplification methods but provides a relatively large region of sequence for optimal probe design. For most sample preparations this gives satisfactory results, however, sample preparations that contain large amounts of degraded or fragmented RNA resulting from the method of preparation or from environmental exposure of the sample, may be difficult to analyze using such an array. If an RNA is fragmented at a point 3' of the region that a probe is complementary to then that probe will not generate signal from that target. During a 3' based amplification scheme a primer is extended from the 3' end of the transcript to the 5' end to make first strand cDNA. If the first strand cDNA is prematurely terminated because of a strand break in the target then any region 5' of the break will not be amplified. In a preferred embodiment of the disclosed invention probes for an array are designed based on the sequence of the MRNA that is within about 300 bases proximal to the 3' end of the mRNA. The probe selection region for each target mRNA is selected to be bound on the 3' end by the 5' end of the poly(A) tail and to extend 300 bases 5' of that 3' boundary.

For any given MRNA there preferably are a plurality of different probes that hybridize to the target, for example, there may be 2 to 16 probe pairs for a single mRNA target. The probe pairs or probes directed at a given target make up a probe set for that target. In a preferred aspect there are 8, 9, 10, 11 or 12 probe pairs for each target. If probe pairs are used, perfect match and mismatch probes, the probe set would thus include 16, 18, 20, 22 or 24 probes. In some aspects different targets may have different numbers of probe pairs, for example, for some targets being interrogated by the array there may be 11 probe pairs, for other targets being interrogated by the array there may be 9, 10 or 12 probe pairs. A probe pair is the perfect match probe and the corresponding mismatch probe. In some aspects all or some of the probe sets include only perfect match probes and mismatch probes are not used. In a preferred aspect the mismatch probe is identical to the perfect match probe except for the central position which is a different base that is not complementary to the target at that position. For example, in a 25 mer probe the $13^{th}$ base is the mismatch position.

Arrays for use with samples that may have some degree of degradation such as formalin fixed paraffin embedded (FFPE) samples may be designed to improve detection of degraded samples. Biopsy samples from tumors are routinely stored after surgical procedures by FFPE, which may compromise DNA and RNA integrity. In a preferred embodiment the probes of the array are designed to hybridize to a region of the mRNA that is within 300 bases of the 3' end of the mRNA (probe selection region). In some aspects the probe selection region is the 200, 350, 400, or 500 bases immediately 5' of the poly(A) tail.

Recent advances in laser-capture microdissection (LCM) facilitate the investigation of cancer by allowing isolation of pure cell populations that can be evaluated for changes in gene expression or genomic material that accompany the development of cancer. Methods to extract high-quality genetic material from archived clinical samples have been limited though, resulting in samples that may be difficult to analyze by microarray based methods. Fine needle aspiration or ductal lavage, for example, may be used to obtain samples of cells from a tissue of interest. Ductal lavage is a washing procedure that can identify cancerous and precancerous cells in the milk ducts of the breast. The procedure involves threading a hair-thin catheter into the duct opening in the nipple, infusing a saline solution through the catheter into the duct and sucking the saline solution and some cells back out. The cells are collected and analyzed. Microdissection may also be used to obtain sample. Reagent kits, for example, the Paradise Reagent System from Arcturus, have been developed to facilitate analysis of FFPE samples.

In many methods of gene expression analysis the MRNA is amplified prior to hybridization using a method of amplification that is biased toward amplification of the 3' end. For example, mRNA may be reverse transcribed using an primer containing a 3' oligo dT region and a 5' phage promoter sequence, (T7, T3, SP6 for example). The first strand cDNA is then used as template for second strand cDNA synthesis resulting in a double stranded cDNA with a promoter for an RNA polymerase. Multiple copies of antisense RNA may be transcribed. These may be labeled and used for hybridization to an array. This amplification method is typically biased toward amplification of the 3' end of the MRNA since reverse transcription is primed from the 3' end. The amount of bias may be increased for mRNAs that are longer. Amplification methods that prime amplification from the 3' end of mRNAs also result in reduced amplification of mRNAs that have been degraded. For example, if an mRNA has been fragmented into two portions, a 5' portion and a 3' portion, only the 3' portion which carries the poly A tail will be amplified. The amplification products won't hybridize to any probes that are 5' of the break in the mRNA. To minimize the loss of signal do to degradation an array with probes designed to be closer to the 3' end of the mRNA are disclosed.

The arrays disclosed herein are particularly well suited for whole-genome expression profiling of formalin-fixed, paraffin embedded (FFPE) samples or other samples that may be compromised or more degraded than a normal sample used for expression analysis, for example, archived samples or forensic samples. In one aspect the arrays disclosed herein may be used to hybridize samples prepared using the Paradise™ Reagent System from Arcturus for expression analysis of FFPE samples.

FFPE samples introduce unique challenges for microarray analysis, including potential fragmentation and chemical modification of RNA molecules. In order to overcome these challenges, the Paradise Reagent System was developed to provide RNA isolation and amplification reagents optimized for FFPE samples. The resulting amplified RNA may be analyzed by hybridization to an array designed to focus on interrogating sequences located closer to the 3' end of the transcripts compared with standard arrays. Together, the reagents and array accommodate the characteristics of the FFPE RNA samples, enabling genome-wide profiling.

In one aspect the target sequences on the array are identical to those used for designing the GeneChip Human Genome U133 Plus 2.0 Array, for a total of more than 47,000 transcripts with more than 61,000 probe sets, although the probes on the two types of arrays are significantly different. The probe selection criteria for the arrays disclosed herein are modified to accommodate the unique characteristics of FFPE samples. The probe selection region in one aspect is restricted to the 300 bases at the most 3' end of the transcripts immediately upstream of the poly(A) tail. In contrast, the design strategy for other arrays employed selection of probe sets within the region 600 bases proximal to the 3' ends of targets.

In some aspects some targets were not amenable to selection of high-performance probe sets within the shorter probe selection region and for approximately 4,000 transcripts, two sets of probe sets were selected for an array 1) the original probe sets from the standard HG-U133 Plus 2.0 Array design, and 2) a new, more 3' probe set that did not meet the minimum probe score selection threshold but is more biased toward the 3' end. In addition, for fewer than 200 transcripts where no probe sets within the smaller (300 bps) probe selection region could be found, only the HG-U133 Plus 2.0 Array probe sets are represented on the array.

Oligonucleotide probes are synthesized in situ complementary to each corresponding sequence. For many target sequences eleven pairs of oligonucleotide probes are used to measure the level of transcription of each sequence represented. Each probe is synthesized in a different feature of the array or associated with a different feature of the array and the location of the probes is known or determinable. In some aspects each probe is attached to a bead and the array is an array of beads. The beads may be associated with a solid support in a manner that allows determination of the location of different probe sequences, for example, through marking each bead or probe with a detectable marker such as a tag. The tag may be a sequence associated with the probe.

Preferred arrays have more than 100,000, more than 500,000, more than 1,000,000, more than 5,000,000 or more than 10,000,000 different features or probes. However, arrays with fewer probes are also contemplated. For example, arrays with 1,000 to 2,000, 2,000 to 5,000 or 5,000 to 100,000 probes are contemplated. In some aspects arrays are designed to interrogate a selected set of transcripts. The transcripts for interrogation may be from genes that have been associated with a particular disease state, for example genes that are known to be differentially expressed in a particular type of cancer, a particular stage of cancer, or associated with a particular treatment outcome. Gene expression profiles have been identified that are associated with, for example, breast cancer, prostate cancer, and lung cancer or with different stages or treatment outcomes of these cancers. Gene expression profiles that are associated with many different cancers or disease states have been identified by researchers and are continually being identified and further refined. Arrays that target a subset of genes which may be measured to diagnose, stage or predict treatment outcome are contemplated. The arrays, preferably would target the region 300 bases upstream of the poly A site as a probe selection region. Preferably all of the probes of a probe set for a selected target are complementary to a region within the probe selection region.

In a preferred aspect the arrays disclosed herein include a plurality of control probes. Control probes may include, for example, probes to a plurality of different human maintenance genes. The maintenance genes may be used to facilitate the normalization and scaling of array experiments. In a preferred aspect the control probe sets are the same as the control probe sets on the HG-U133 Plus 2.0 Array. This set of genes serves as a tool to normalize or scale your data prior to performing data comparison. This set of normalization genes shows consistent levels of expression over a diverse set of tissues. Mask files enabling the use of these probe sets for normalization and scaling are available on the Affymetrix web site.

In a preferred embodiment the array is designed to detect human genes, but arrays may be designed using the disclosed methods to detect expression of any organism, for example, rat, mouse, fly, Arabidopsis, yeast, E. coli, bovine, chicken and zebra fish.

In a preferred embodiment the array is designed to detect more than 40,000 different transcripts from human. Other human arrays and methods of using human arrays are disclosed in U.S. patent application Ser. No. 10/355,577 (publication No. 20030198983A1), U.S. Ser. Nos. 09/953, 115, 10/098,263, and 09/660,222 the disclosures of which are incorporated herein by reference in their entireties for all purposes.

Other methods of making or using arrays or of preparing samples for analysis are disclosed in U.S. Pat. Nos. 6,610,482, 6,576,424 and 6,506,558, and in U.S. patent publication No. 20050014168 which are incorporated herein by reference in their entireties. In some aspects arrays are designed to target alternatively spliced products.

In addition to arrays the invention also provides articles of manufacture such as kits for the practice of the methods of the invention. In a preferred aspect the kits contain a reagent set comprising buffers, primers and enzymes ready to load into one or more reaction tubes along with extracted or amplified nucleic acid samples, as a non-limiting example. The sequences of the primer or primers preferably comprise a sequence that is complementary to the 3' region of one or more cellular transcripts, oligo dT for example, and capable of quantitatively amplifying sequences within the 3' region as described herein. In another aspect the reagent set is packaged in a kit with one or more arrays as disclosed herein. The reagent set may be optimized for amplification of the 300 bases immediately 5' of the polyA tail of mRNA. A kit according to the present invention also preferably comprises suitable packaging material. Preferably, the packaging includes a label or instructions for the use of the article in a method disclosed herein.

EXAMPLE 1

The GeneChip X3P array was designed for whole genome analysis of degraded samples, such as FFPE samples. The array comprises a plurality of individual features. An oligo of known sequence is synthesized in each feature of the array. Each of SEQ ID NOs: 1-673,904 is present on the array in a different feature on the array, for example, there is a feature that comprises multiple copies of SEQ ID NO: 1 and a second feature the includes multiple copies of SEQ ID NO: 2 and so on. The feature may also include prematurely terminated probes. The location of the features and the sequence of the oligonucleotides present at each feature are known. A nucleic acid sample is obtained and prepared using the Paradise Reagent System from Arcturus. The labeled sample is hybridized to the array according to the protocol provided in the Affymetrix GeneChip Expression Analysis Technical Manual Rev. 5 (PN 701021) which is incorporated herein by reference in its entirety for all purposes. The hybridization pattern is analyzed and relative levels of expression for different transcripts can be determined. Exogenously added controls and endogenous transcripts may be used to normalize expression measurements between samples.

CONCLUSION

It is to be understood that the above description is intended to be illustrative and not restrictive. Many variations of the invention will be apparent to those of skill in the art upon reviewing the above description. The scope of the invention should be determined with reference to the appended claims, along with the full scope of equivalents to which such claims are entitled. All cited references, including patent and non-patent literature, are incorporated herewith by reference in their entireties for all purposes.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07374927B2). An electronic copy of the "Sequence Listing" will also be available from the USPTO upon request and payment of the fee set forth in 37 CFR 1.19(b)(3).

We claim:

1. An array comprising a plurality of different sequence oligonucleotide probes wherein each different sequence in the plurality consists of one of the sequences in SEQ ID NO: 1-673,904, wherein the plurality of different sequence oligonucleotide probes consists of each of the sequences listed in SEQ ID NO: 1-673,904 and wherein each different sequence is present in a different feature of the array.

2. The array of claim 1 further comprising a plurality of control probe sets.

3. The array of claim 1 wherein the array comprises a plurality of beads or particles each having a single sequence from SEQ ID NO: 1-673,904 attached and wherein the array includes at least one bead having each of the sequences listed in SEQ ID NO: 1-673,904 attached.

4. The array of claim 3 wherein the plurality of beads is associated with a solid support to form an array of beads.

* * * * *